United States Patent
Aiken et al.

(10) Patent No.: US 10,940,090 B2
(45) Date of Patent: Mar. 9, 2021

(54) SYRINGE ASSEMBLY

(71) Applicant: Veriton Pharma Limited, Surrey (GB)

(72) Inventors: Hannah Aiken, Surrey (GB); Chris Grimes, Surrey (GB); Aaron Hirschmann, Lake Geneva, WI (US); Robert Fesus, Lake Geneva, WI (US)

(73) Assignee: Veriton Pharma Limited, Surrey (GB)

( * ) Notice: Subject to any disclaimer, the term of this patent is extended or adjusted under 35 U.S.C. 154(b) by 106 days.

(21) Appl. No.: 15/516,004

(22) PCT Filed: Oct. 2, 2015

(86) PCT No.: PCT/GB2015/052891
§ 371 (c)(1),
(2) Date: Mar. 30, 2017

(87) PCT Pub. No.: WO2016/051200
PCT Pub. Date: Apr. 7, 2016

(65) Prior Publication Data
US 2017/0296434 A1    Oct. 19, 2017

(30) Foreign Application Priority Data

Oct. 3, 2014   (GB) .................................... 1417545

(51) Int. Cl.
*A61J 7/00*      (2006.01)
*A61M 5/31*     (2006.01)

(52) U.S. Cl.
CPC .... *A61J 7/0053* (2013.01); *A61M 2005/3104* (2013.01)

(58) Field of Classification Search
CPC .................... A61J 7/0053; A61M 5/28; A61M 2005/3104; A61M 2005/3117;
(Continued)

(56) References Cited

U.S. PATENT DOCUMENTS

| 868,450 A | 10/1907 | Kistler |
| 1,712,070 A * | 5/1929 | Cressler ................. A61M 5/24 604/237 |

(Continued)

FOREIGN PATENT DOCUMENTS

| CN | 201750930 U | 2/2011 |
| EP | 1779882 A2 * | 5/2007 .......... A61M 5/3129 |

(Continued)

OTHER PUBLICATIONS

"Toward." Merriam-Webster.com. 2019. https://www.merriam-webster.com (Year: 2019).*

*Primary Examiner* — Scott J Medway
(74) *Attorney, Agent, or Firm* — Pokalsky Wilczynski Brozek LLP

(57) ABSTRACT

A syringe assembly (2) comprises a syringe barrel (4) comprising an inner chamber (14) filled or adapted to be filled with medicament, and a channel (18) in fluid communication with the chamber and through which medicament is dispensed. The assembly further comprises an outer sheath (6) configured to be removably attached to the syringe barrel, and comprising a projection (40) which is received by the channel when the outer sheath is attached to the barrel, thereby creating a seal, which prevents medicament from flowing therethrough.

20 Claims, 9 Drawing Sheets

(58) Field of Classification Search
CPC .......... A61M 5/347; A61M 2005/3261; A61M 5/344; A61M 2005/3247; A61M 5/3129
See application file for complete search history.

(56) References Cited

U.S. PATENT DOCUMENTS

| | | | | |
|---|---|---|---|---|
| 3,673,411 | A * | 6/1972 | Glasser | A61M 5/1785 250/506.1 |
| 4,636,202 | A | 1/1987 | Lowin | |
| 4,752,290 | A * | 6/1988 | Schramm | A61M 5/3243 604/198 |
| 5,318,547 | A * | 6/1994 | Altschuler | A61M 5/315 604/198 |
| 5,342,320 | A * | 8/1994 | Cameron | A61M 5/3257 604/192 |
| 6,344,031 | B1 * | 2/2002 | Novacek | A61L 2/28 604/110 |
| 6,425,174 | B1 * | 7/2002 | Reich | G21F 5/018 29/469 |
| 7,028,837 | B2 * | 4/2006 | Yanke | A61J 1/00 206/364 |
| 7,118,552 | B2 * | 10/2006 | Shaw | A61M 5/326 604/110 |
| 7,455,661 | B2 * | 11/2008 | Barrelle | A61M 5/326 604/187 |
| 7,497,390 | B2 * | 3/2009 | Beller | A61M 11/02 239/333 |
| 10,850,085 | B2 * | 12/2020 | Tekeste | A61M 39/16 |
| 2004/0178163 | A1 * | 9/2004 | Kerns | A61J 1/1406 215/11.1 |
| 2005/0113764 | A1 * | 5/2005 | Watkins | A61M 5/3243 604/197 |
| 2005/0224730 | A1 * | 10/2005 | Fago | G21F 5/018 250/507.1 |
| 2006/0095010 | A1 * | 5/2006 | Westbye | A61M 5/326 604/197 |
| 2006/0106349 | A1 * | 5/2006 | Kito | A61M 5/344 604/187 |
| 2008/0086092 | A1 * | 4/2008 | Loe | A61M 5/1785 604/198 |
| 2009/0292157 | A1 * | 11/2009 | Bruce | A61M 5/1785 600/5 |
| 2012/0016314 | A1 * | 1/2012 | Tachikawa | A61M 5/31515 604/222 |
| 2012/0109072 | A1 * | 5/2012 | Tabata | A61M 5/28 604/192 |
| 2014/0052074 | A1 * | 2/2014 | Tekeste | A61M 5/31 604/199 |
| 2016/0082194 | A1 * | 3/2016 | Furukawa | A61M 5/31513 604/222 |
| 2019/0298986 | A1 * | 10/2019 | Rivier | A61M 5/3134 |

FOREIGN PATENT DOCUMENTS

| | | |
|---|---|---|
| GB | 2336541 A | 10/1999 |
| WO | 97/04733 A1 | 2/1997 |

* cited by examiner

SYRINGE ASSEMBLY

This application is a 371 application of PCT/GB2015/052891, filed Oct. 2, 2015, the contents of which are incorporated by reference herein.

The present invention relates to syringe assemblies, and particularly, although not exclusively, to syringe assemblies for storing and dispensing a medicament. In particular, the syringe assemblies are configured to administer liquid medicament buccally, orally, sublingually, rectally, vaginally, topically and/or transdermally. The invention extends to methods of using the syringe assemblies for the delivery of medicament.

Pharmaceutical compositions may be administered to patients via a range of routes including orally, buccally, sublingually, rectally, vaginally, topically and/or transdermally. These routes of administration are advantageous as drugs administered in this way may be absorbed through the mucous membranes, or Stratum corneum and skin layers associated with the sites of delivery. Buccal and sublingual delivery is further advantageous over orally administered medicament as this avoids hepatic first pass metabolism and drugs are not exposed to acidic degradation in the stomach or to enzymatic degradation within the gastrointestinal (GI) tract.

As a result of the benefits provided by administration via the buccal and sublingual route, there has been considerable interest in reformulating drugs which have conventionally been administered by other routes. Additionally, a number of drugs formulated for administration by other routes, such as injectable solutions, have been used to treat patients buccally, for example morphine, midazolam and diamorphine. An example of such a product is Epistatus, which is a composition comprising midazolam (Special Products Limited, UK).

Traditionally, liquid medicaments administered orally, buccally and sublingually may be administered using a syringe or cup being dispensed from a bottle, ointment or an oral spray. However, a medicament may only be administered orally if the patient is cooperative, and this may not always be possible. For example, buccal midazolam is used to treat epileptic patients who are suffering from seizures, and especially prolonged acute convulsive seizures. Accordingly, a patient suffering from a seizure would not be able to cooperate. When a patient is suffering from a seizure, they may bite down, which would make it even harder to administer an oral medicament. Finally, an oral spray will also have draw backs associated with it, as it will be difficult to administer to an uncooperative patient and the patient could inadvertently inhale the spray.

Previously, syringes have been used to administer medicaments buccally, sublingually and orally. In this case, the medicament would generally be provided as a bulk liquid, and a dose of the liquid would be drawn into the syringe or cup and administered to the patient. However, preparing doses in this way can result in an incorrect dose being erroneously drawn from the bulk liquid. Additionally, a number of drugs which are administered buccally are controlled substances. As a requirement of legislation in most countries, access to bulk supplies of such drugs is carefully managed. If a patient is in urgent need of the drug, locating and accessing the bulk supply of the drug will add to the time required to calculate, obtain, prepare and administer the dose.

A further drawback is that once a syringe has been filled and is being taken to the patient, a relatively low amount of pressure on the plunger end of the syringe will result in inadvertent discharge of the medicament. Additionally, most syringes are configured to allow connection to a needle or drip. In practice this generally means that syringes are provided with a screw thread or projection adjacent to the tip which can be connected to a transfer means such as a needle or a drip. When used to administer medicament buccally, this screw thread or projection could cause damage the mucous membrane in a patient's cheek.

Finally, a dose of a medicament intended for buccal administration would often be harmful if it were injected intramuscularly or intravenously. The use of a syringe to deliver the medicament could lead to confusion on the part of the administrator resulting in them administering the medicament via the incorrect route. In a worst case scenario can result in the death of the patient.

The present invention arises from the inventor's work in trying to overcome the problems associated with buccal administration in the prior art.

In accordance with a first aspect of the invention, there is provided a syringe assembly comprising:
  a syringe barrel comprising an inner chamber filled or adapted to be filled with medicament, and a channel in fluid communication with the chamber and through which medicament is dispensed; and
  an outer sheath configured to be removably attached to the syringe barrel, and comprising a projection which is received by the channel when the outer sheath is attached to the barrel, thereby creating a seal, which prevents medicament from flowing therethrough.

Advantageously, the projection on the outer sheath creates a first seal allowing a medicament to be stored within the inner chamber of the syringe, and preventing leakage or discharge of the medicament, and evaporation of any solvent when the outer sheath is attached to the barrel.

Preferably, the projection comprises a length of at least 1 mm. More preferably, the projection comprises a length of at least 2 mm or 3 mm. Most preferably, the projection comprises a length of at least 4 mm.

Preferably, the syringe barrel and outer sheath each comprise engagement means which are configured to mutually engage with each other in order to create a second seal, which prevents leakage or discharge of the medicament from the chamber when the outer sheath is attached to the barrel.

Preferably, the engagement means is disposed on an external surface of the syringe barrel, preferably at least adjacent or towards the end of the barrel, which is opposite to that from which medicament is dispensed. Preferably, the engagement means is disposed on an internal surface of the outer sheath, preferably at least adjacent or towards the end of the outer sheath, which is opposite to that from which medicament is dispensed. Preferably, the engagement means comprise screw threads. Hence, preferably the outer sheath is configured to be removably attached to the barrel due to the corresponding screw threads provided on the cap and the barrel.

Advantageously, the two screw threads work in combination with the first seal created by the projection on the cap which blocks the channel to create a second seal or double gasket (i.e. two seals). Additionally, since the screw threads provided on the external surface of the barrel are spaced apart from the end of the assembly from which medicament is dispensed, they cannot cause any damage to the buccal cavity of a patient. The inventors therefore believe the provision of the screw threads is novel per se.

In accordance with a second aspect, there is provided a syringe assembly comprising:

a syringe barrel comprising an inner chamber filled or adapted to be filled with medicament, and a channel in fluid communication with the chamber and through which medicament is dispensed; and an outer sheath configured to be removably attached to the syringe barrel, wherein the syringe barrel and outer sheath each comprise a screw thread, which are configured to mutually engage with each other in order to create a seal, which prevents medicament from flowing through the channel.

Preferably, the screw thread is disposed on an external surface of the syringe barrel, preferably at least adjacent or towards the end of the barrel, which is opposite to that from which medicament is dispensed. Preferably, the screw thread is disposed on an internal surface of the outer sheath, preferably at least adjacent or towards the end of the outer sheath, which is opposite to that from which medicament is dispensed.

Preferably, the outer sheath comprises a projection which is received by the channel when the outer sheath is attached to the barrel, thereby creating a second seal, which prevents medicament from flowing therethrough. Preferably, the projection comprises a length of at least 1 mm, more preferably at least 2 mm or 3 mm, and most preferably at least 4 mm.

Thus, preferably the screw threads (first seal) work in combination with the projection on the cap which blocks the channel which creates a second seal or double gasket (i.e. two seals).

Preferably, the syringe assembly of the first or second aspect of the invention is a syringe assembly for administering medicament orally, buccally, sublingually, rectally, vaginally, topically or transdermally. Most preferably, however, the syringe assembly is a buccal syringe assembly, which is used for administering medicament to a patient's buccal cavity.

Preferably, the syringe barrel does not comprise attachment means for connection to a medicament transfer means. An attachment means may comprise anything which is configured to allow a medicament transfer means to be attached thereto, thereby enabling the flow of medicament from the chamber and into the transfer means. An attachment means may include a projection and/or screw thread disposed at least adjacent to the end of the syringe barrel from which medicament is dispensed, and configured to be attached to a transfer means. Preferably, therefore, the syringe barrel is incompatible with a Luer lock, or a Luer slip, and the like. For example, a medicament transfer means may include anything that is configured to be attached to the syringe barrel for the transfer of the medicament from the syringe barrel to a patient, such as a needle or a drip.

Preferably, the syringe barrel of the invention does not comprise an external screw thread at least adjacent or towards the end of the barrel from which medicament is dispensed, i.e. on the delivery tip. Accordingly, the syringe barrel cannot cause any damage to the buccal cavity of a patient.

Advantageously, this safety mechanism ensures that it is not possible to use the syringe assembly of the invention to administer the medicament intravenously or intramuscularly, which could otherwise cause harm to a patient and might even result in their death.

Preferably, the end of the barrel from which medicament is dispensed is substantially rounded or smooth. This feature ensures that the risk of damage occurring to the patient's buccal cavity is reduced.

Preferably, the end of the barrel from which medicament is dispensed comprises a plurality of spaced apart flanges, which extend from a side wall of the barrel and converge at the dispensing tip of the barrel to define an aperture which leads to the channel through which medicament is dispensed. Preferably, the flanges are equally spaced apart. Most preferably, the flanges have a curved profile. Preferably, adjacent flanges are the same length so as to produce a substantially smooth profile. Preferably, the end of the barrel from which medicament is dispensed comprises at least two, three, four, five or six flanges. Most preferably, the end of the barrel from which medicament is dispensed comprises four flanges. Advantageously, this number of flanges provides a smooth outer surface which is presented to the patient's internal cavity, such as mouth.

Advantageously, the flanges prevent air pockets from forming in the barrel during the manufacturing process, while allowing the barrel to withstand the force of a human bite. This is especially advantageous if the syringe assembly is used to treat a patient suffering from a seizure or fit.

Preferably, the barrel comprises a transparent or translucent material. The barrel may comprise any polymer that may be injection moulded, such as polypropylene, low density polyethylene (LDPE), high density polyethylene (HDPE), polycarbonate, thermoplastic elastomers, cyclic olefin polymer, cyclic olefin copolymer and blended materials thereof.

Preferably, the outer sheath is configured to be removably attached to the syringe barrel to thereby encase at least a portion of the chamber, and preferably all of the chamber. Preferably, the outer sheath comprises an opaque material and/or an amber coloured material. Advantageously, the outer sheath prevents the medicament from being exposed to light when it is contained within the chamber inside the barrel. The outer sheath may be manufactured by injection moulding plastics such as polypropylene, LDPE, HDPE, polycarbonate, thermoplastic elastomers, cyclic olefin polymer, cyclic olefin copolymer and blended materials thereof.

Preferably, the diameter of the outer sheath for the majority of its length is between 5 mm and 30 mm, more preferably, between 7.5 mm and 20 mm or between 10 mm and 15 mm, most preferably, between 12 mm and 13 mm. The term "majority of its length" can mean at least 60%, 70% or at least 80% of the sheath's length, preferably at least 90% of the length of the sheath.

In one embodiment, an external surface of the outer sheath is substantially smooth. In an alternative embodiment, an external surface of the sheath comprises one or more projection which extends transversely therefrom, and which is configured to facilitate removal of the outer sheath from the barrel. Preferably, the outer sheath comprises a plurality of spaced apart elongate ridges or protrusions, which extend along the longitudinal axis of the outer sheath. Preferably, the outer sheath comprises at least two, three or four spaced apart elongate ridges or protrusions. Preferably, the elongate ridges or protrusions extend at least 1 mm above the surface of the outer sheath. More preferably, the elongate ridges or protrusions extend at least 2 mm, 3 mm, 4 mm or 5 mm above the surface of the outer sheath. Most preferably, the elongate ridges or protrusions extend at least 6 mm, 7 mm or 8 mm above the surface of the outer sheath. In yet an alternative embodiment, at least a portion of the external surface of the outer sheath comprises a softened material. Preferably, the softened material comprises rubber or a suitable thermoplastic elastomer.

Advantageously, the ridges, protrusions or the softened material allows a user to better grip the outer sheath to aid in its removal from the barrel.

Preferably, the outer sheath comprises a circumferential band at least adjacent to the end of the outer sheath, which is opposite to that from which medicament is dispensed, the band being configured to increase the diameter of the outer sheath. The circumferential band is preferably configured to increase the diameter of the outer sheath by at least 5%, more preferably, at least 10%, 15%, 20% or 25% most preferably, at least 35%.

Advantageously, the band enables the outer sheath to be manufactured more easily.

In one embodiment, the syringe assembly is a single unit dose syringe assembly pre-filled with medicament. Preferably, the medicament is selected from a group of medicaments consisting of: analgesics, anti-convulsants, antidepressants, vasodilators, steroids, opiate antagonists, anaesthetics, antiadrenergic compounds, antiallergic drugs, anti-anginals, anti-asthmatics, antibacterials, anti-coagulants, anti-cholinergics, antiemetics, antiepileptics, antihistaminics, antiinfectives, antiinflammatories, antimigraine drugs, bronchodilators, cardiac depressants, thrombolitics, beta blockers, opioids, sedatives, benzodiazepines and stimulants.

More preferably, the medicament is selected from a group consisting of: midazolam, lorazepam, diazepam, paraldehyde, pentobarbital, morphine, carbamazepine, ethosuximide, clorazepate, clonazepam, felbamate, forphenytoin, gabapentin, lacosamide, lamotrigine, levetiracetam, oxacarbacepine, phenobarbital, phenytoin, pregabalin, primidone, tiagabine, topiramate, zonisamide, clobazam, vigabatrin, fentanyl, oxycodone, diamorphine, alprazolam, clonazepam, vasopressin, levetiracetam, and NSAIDs, or a salt thereof.

Most preferably, the syringe assembly is a unit dose syringe assembly pre-filled with midazolam or a salt thereof, such as midazolam maleate.

Preferably, the syringe assembly comprises a plunger configured to slide in the chamber. The plunger can be manufactured by injection moulding plastics. The plunger may suitably be moulded from polypropylene, LDPE, HDPE, polycarbonate, thermoplastic elastomers, cyclic olefin polymer, cyclic olefin copolymer and blended materials thereof.

Preferably, the plunger comprises a rod having first and second ends, wherein the first end is inserted into the chamber, and the second end comprises a thumb tab, and the barrel comprises a finger tab, which is configured to be engaged with the finger of one hand while also engaging the thumb tab with the thumb of the same hand. Hence, preferably the syringe is configured such that when the outer sheath is detached from the barrel, a user may apply pressure to the finger and thumb tabs, which causes the plunger rod to slide within the chamber and causing the medicament to be dispensed through the channel.

Preferably, the finger tab is disposed at least adjacent to, or towards, the end of the barrel, which is opposite to that from which medicament is dispensed. More preferably, the finger tab is disposed adjacent to the end of the barrel, which is opposite to that from which medicament is dispensed. Preferably, the finger tab extends in a direction substantially perpendicular to the longitudinal axis of the barrel. Preferably, the finger tab extends from at least two sides of the barrel. Preferably, the two sides comprise opposite sides. Preferably, the finger tab is configured to be accessible when the outer sheath is attached to the syringe barrel. Preferably, the finger tab is sized to extend beyond the diameter of the outer sheath. Preferably, the finger tab has a maximum width of at least 12 mm. More preferably, the finger tab has a maximum width of at least 13 mm, 14 mm, 15 mm, 16 mm, 17 mm, 18 mm, 19 mm or 20 mm. Most preferably, the finger tab has a maximum width of at least 21 mm, 22 mm, 23 mm, 24 mm or 25 mm.

Preferably, the maximum width of the finger tab is at least 50% greater than the width of the barrel. More preferably, the maximum width of the finger tab is at least 60%, 70% or 80% greater than the width of the barrel. Most preferably, the maximum width of the finger tab is at least 100%, 120, 140 or 160% greater than the width of the barrel.

Preferably, the maximum width of the finger tab is at least 10% greater than the width of the outer sheath adjacent to the end of the outer sheath, which is opposite to that from which medicament is dispensed. More preferably, the maximum width of the finger tab is at least 20%, 30%, 40% or 50% greater than the width of the outer sheath adjacent to the end of the outer sheath, which is opposite to that from which medicament is dispensed. Most preferably, the maximum width of the finger tab is at least 60% or 70% greater than the width of the outer sheath adjacent to the end of the outer sheath, which is opposite to that from which medicament is dispensed.

Preferably, the pre-loaded single unit dose syringe assembly is configured to dispense substantially all of the medicament in a single delivery. Preferably, the syringe assembly comprises a transversely extending projection disposed on the side of the plunger rod, and an indentation disposed along the inside of the chamber, or vice versa, wherein alignment of the projection and indentation correlates with a defined volume of medicament and thereby a dosage. Hence, the plunger rod is maintained at the fill volume when not stored. The advantage of the stop therefore helps to ensure that an accurate dosage of medicament is inserted into the chamber during loading. It also stops the plunger rod from being withdrawn from the barrel.

Accordingly, in a preferred embodiment the syringe assembly may be configured to deliver the required different single doses. For example, the plunger can be arranged to deliver 0.25 ml, 0.5 ml, 0.75 ml or 1 ml medicament.

Hence, in some embodiments the chamber is preferably adapted to hold about 0.1-25 ml of medicament, or more preferably about 0.1-25 ml, or about 0.1-10 ml, or about 0.1-5 ml, or about 0.1-2 ml, or about 0.1-1 ml of medicament.

In a third aspect, there is provided the syringe assembly of the first aspect or second aspect, for use in therapy.

In a fourth aspect, there is provided the syringe assembly of the first aspect or second aspect, for use in treating, preventing or ameliorating a seizure.

In accordance with a fifth aspect, there is provided midazolam or a salt thereof, for use in treating a seizure, wherein the midazolam is for buccal administration using the syringe assembly according to the first or second aspect.

The seizure may be a prolonged acute convulsive seizure, which could result in status epilepticus.

In accordance with a sixth aspect, there is provided morphine, for use in treating pain, wherein the morphine is for buccal administration using the syringe assembly according to the first or second aspect.

In accordance with a seventh aspect, there is provided a method of administering a medicament to a patient in need of treatment using a syringe assembly according to the first or second aspect, the method comprising removing the outer sheath from the barrel; and dispensing medicament from the chamber, to thereby administer the medicament to the patient.

Preferably, the syringe assembly of the first or second aspect of the invention is used to administer the medicament orally, buccally, sublingually, rectally, vaginally, topically or transdermally. However, buccal administration is preferred.

Hence, according to an eighth aspect, there is provided a method of administering a medicament to a patient in need of treatment using a syringe assembly according to the first or second aspect, the method comprising: removing the outer sheath from the barrel; inserting an end of the barrel into a bodily cavity of a patient in need of treatment; and applying pressure to a plunger, thereby causing medicament contained in a chamber to be dispensed.

All features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:

FIGS. 1a-d show side views of various embodiments of a syringe assembly according to the invention. Each embodiment of the syringe assembly has a slidable plunger disposed in a barrel, which is shown encased by a different design of a covering sheath or cap. For example, the outer cap shown in FIG. 1a is ridged, whereas the FIG. 1b cap is soft, the FIG. 1c cap has finger grips, and the FIG. 1d cap is smooth;

FIGS. 2a-d show side views of the outer sheath caps shown in FIGS. 1a-d, but with the syringe removed;

FIGS. 3a and b show enlarged side views of the tip of an embodiment of the syringe assembly encased by the cap (FIG. 3a) and without the cap (FIG. 3b). In this embodiment, the tip of the syringe has four flanges;

FIGS. 4a and b shows enlarged side views of the tip of another embodiment of the syringe assembly with the cap (FIG. 4a) and without the cap (FIG. 4b). In this embodiment, the syringe tip has six flanges;

EXAMPLE

Figure 1A:
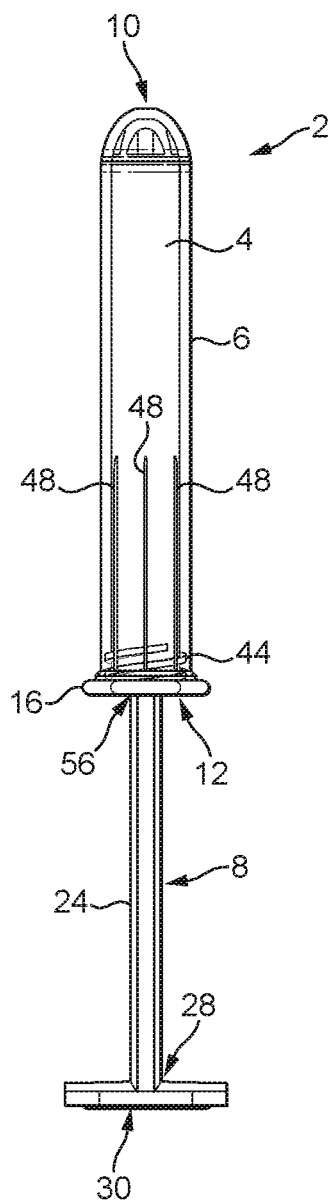

The inventors have designed a novel syringe assembly 2, which is shown in the Figures. The syringe assembly 2 is primarily used for the buccal delivery to a patient of medicament, such as Epistatus, which is a composition comprising midazolam maleate (Special Products Limited, UK).

Referring first to FIGS. 1a-d, the syringe assembly 2 generally consists of a main barrel 4 into which a plunger 8 is inserted, and an outer covering cap or sheath 6 which encases the barrel 4, when the syringe is not in use. The outer cap 6 is removed from the barrel 4 prior to administration of the medicament to the patient. The barrel 4 has a smooth rounded first end 10, a flat second end 12 having a finger tab 16, and an inner chamber 14 that extends through the core of the barrel 4 between the first and second ends 10, 12, as most clearly shown in FIGS. 4 and 5. The inner chamber 14 is sized so as to hold a desired volume of medicament, for example about 0.1-10 ml medicament.

Figure 7:
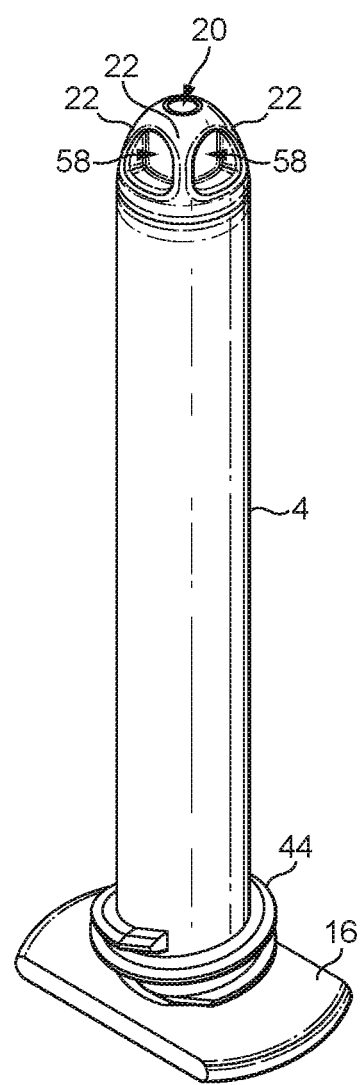
FIG. 7 is a perspective view of a barrel.

An outer finger tab 16 is disposed around the circumference of the second end of the barrel 4, and provides a surface against which a user's fingers can apply pressure. Additionally, the finger tab 16 may be gripped by the user when the cap 6 is removed from the barrel 4. An embodiment with a larger finger tab 16 is shown in FIG. 7. The combined maximum width of the two finger tabs 16 is 17.75 mm. However, the inventors have also envisaged an alternative embodiment (not shown) where the maximum width of the two finger tabs is 25.40 mm. By way of comparison, the external diameter of the barrel 4 is 9.68 mm. Accordingly, in the embodiment illustrated in FIG. 7 the width of the finger tabs 16 is 83% greater than the width of the barrel 4, and in the further embodiment envisaged by the inventors, the width of the finger tabs 16 is 162% greater than the width of the barrel 4. As explained below, the maximum width of the larger finger tabs 16 is greater than the diameter of the cap 6, and they therefore aid the user in removing the barrel 4 from the cap 6, as well as in dispensing the medicament. In use, once the cap 6 has been removed from the barrel 4, medicament (such as midazolam maleate) stored in the chamber 14 is dispensed through an elongate channel 18 which extends between the chamber 14 and the first end 10 of the barrel 4 and out of tip 20, which is shown most clearly in FIG. 4.

Figure 3A:
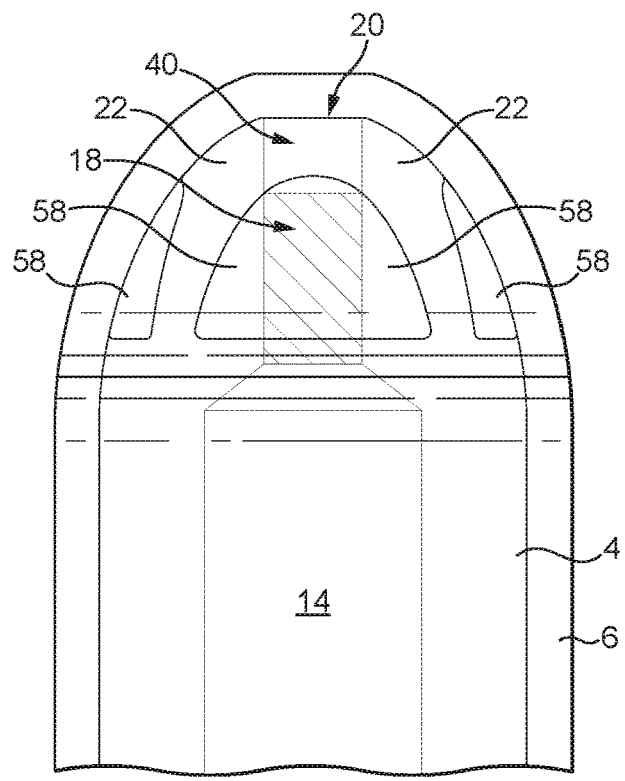
Figure 3B:
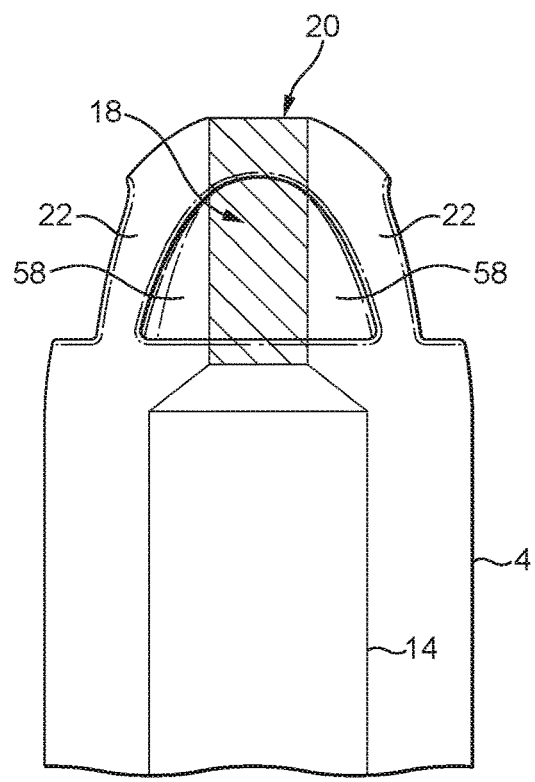
Figure 4A:
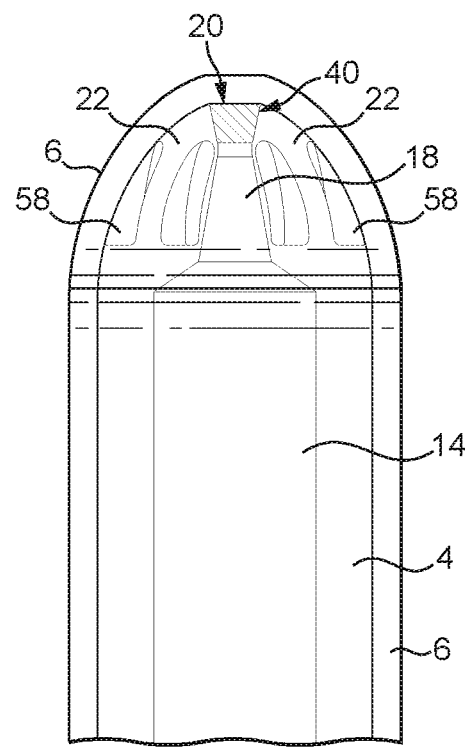
Figure 4B:
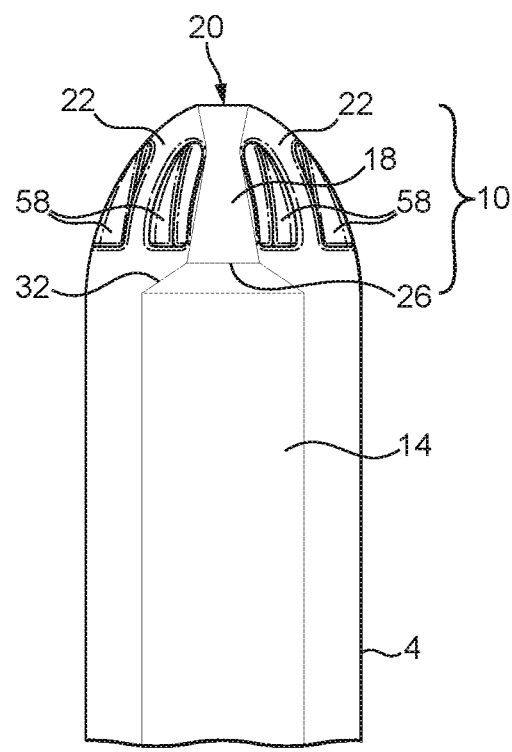

The inventors have found that the thickness of the material of the barrel 4 should ideally be consistent in order to avoid it from cooling at different rates during the manufacturing process, which could result in air pockets forming within the barrel 4, thereby weakening its structure. For this reason, the first end 10 of the barrel 4 comprises a plurality of equally spaced apart flanges 22, which extend radially outwards therefrom. Adjacent flanges 22 are separated by apertures or gaps 58, as shown in FIGS. 3 and 4. The provision of these flanges 22 ensures that the thickness of the material of the barrel 4 is consistent and prevents air pockets from forming during the manufacturing process. In the embodiment shown in FIGS. 3a and 3b, the first end 10 of the barrel 4 has four spaced apart flanges 22 (and corresponding gaps 58), and in FIGS. 4a and 4b, the first end 10 of the barrel 4 has six spaced apart flanges 22 (and corresponding gaps 58). Together these flanges 22 create a substantially smooth and rounded external profile, which reduces the risk of damaging the patient's buccal cavity during drug administration.

Due to the intended use of the syringe assembly 2, the flanges 22, as well as the rest of the barrel 4, must be able to withstand the force of a bite from a patient being buccally administered medicament via the syringe 2. The inventors believe that a barrel 4 where the first end 10 comprises four, five or six flanges 22 is sufficiently robust to withstand a bite. Furthermore, the embodiment where the first end 10 comprises four flanges 22 presents the smoothest external surface and is less likely to cause a lesion in the patient's mouth, and hence is preferred.

The barrel 4 is made of a transparent or translucent material allowing the patient to see the medicament which is to be dispensed from the chamber 14. The barrel 4 can be manufactured by injection moulding plastics, for example polypropylene, LDPE, HDPE, polycarbonate, thermoplastic elastomers, cyclic olefin polymer, cyclic olefin copolymer and blended materials thereof.

Referring to FIG. 1, the plunger 8 comprises an elongated plunger rod 24 having a first end 26 fitted with a rubber or suitable alternative materials plunger tip (not shown), which is inserted into the chamber 14 in the barrel 4, and a second opposing end 28 on which is disposed a thumb tab 30 which is sized so as to be operable by a user's thumb. In use, a user depresses the plunger rod 24 to slide along the chamber 14 by exerting pressure on the finger tab 16 with the fingers of one hand. Simultaneously, pressure is applied on the thumb tab 30 with the thumb of the same hand, thereby urging the thumb tab 30 to move towards the finger tab 16 and causing the rod 24 to slide within the chamber 14. In some embodiments, an internal rubber seal 56 can be disposed at the end of the chamber 14 towards the second end of the barrel 4, which provides a good seal with the rod 24 as it slides along the chamber 14.

In one embodiment, the rod 24 slides within the chamber 14 until the first end 18 of the rod 24 reaches an end stop 32 of chamber 14, as shown in FIGS. 4a and 4b. The rubber stop (not shown) on the end of the rod 24 ensures that medicament is expelled from the chamber 14 through channel 18 and out of tip 20. It should be appreciated that the design of the tip 20 of the syringe 2 is incompatible with a Luer lock or a Luer slip and/or a needle, and thereby removes any risk of the syringe assembly 2 being used to administer the medicament intravenously or via a drip, which could harm the patient.

Figure 5:
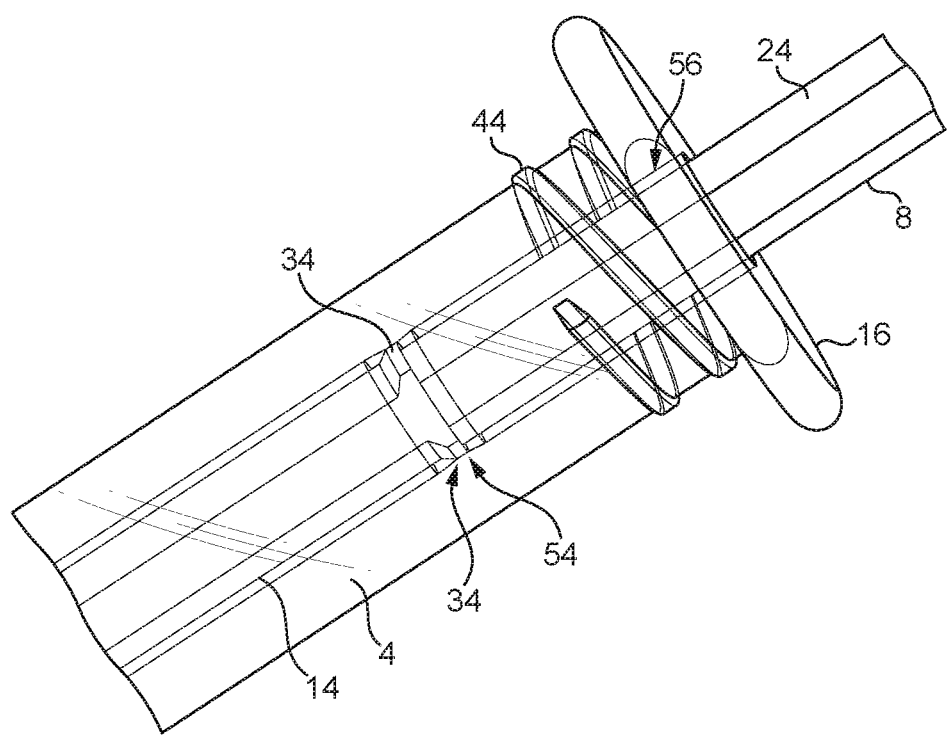
FIG. 5 shows an enlarged cross-sectional side view of the end of a syringe into which the plunger is inserted.

In another embodiment, a transversely extending projection or stop 34 is disposed on the side of the rod 24, and an indentation 54 is disposed along the inside of the chamber 14, as shown in FIG. 5. The stop 34 and indentation 54 help during loading of the assembly 2 with medicament. Alignment of the stop 34 and indentation 54 correlates with a defined volume of medicament and thereby a dosage. Hence, the plunger rod 24 is maintained at the correct fill volume when not stored. The advantage of the stop therefore helps to ensure that an accurate dosage of medicament is inserted into the chamber 14 during loading. It also stops the plunger rod from being withdrawn from the barrel.

For example, the plunger can be arranged to deliver 0.25 ml, 0.5 ml, 0.75 ml or 1 ml medicament. The plunger 8 may be made by injection moulding plastics, for example polypropylene LDPE, HDPE, polycarbonate, thermoplastic elastomers, cyclic olefin polymer, cyclic olefin copolymer and blended materials thereof.

The syringe 2 can be provided pre-filled with medicament, which can be any medicament suitable for buccal administration, such as a composition comprising midazolam. One of the reasons that syringes are not generally provided pre-filled with a medicament is because there are a number of problems associated with the storage of the medicament. For example, if the medicament is light-sensitive, it is important to ensure that it is not exposed to strong light while it is being stored to prevent its degradation. It is also important that a suitable seal is provided to stop the medicament from leaking out of the chamber 14. Additionally, medicaments for buccal administration are often provided in a solvent solution, and so if the seal is not tight enough, then the solvent may evaporate, thereby causing detriment to the quality of the medicament. The syringe 2 illustrated in the Figures overcomes these problems, as described below.

Firstly, as shown in FIGS. 1a-d, the cap 6 is configured to extend substantially over the barrel 4, and it may comprise an opaque material, thereby protecting the medicament stored within the syringe 2 from sunlight. The cap 6 may be made by injection moulding plastics, such as polypropylene, LDPE, HDPE, polycarbonate, thermoplastic elastomers, cyclic olefin polymer, cyclic olefin copolymer and blended materials thereof. In an embodiment, the cap 6 is made of an opaque material which prevents light from damaging the medicament.

Secondly, the cap 6 is configured to create a double gasket-type seal with the barrel 4 of the syringe 2 in order to prevent leakage of the medicament as well as evaporation of ethanol from the chamber 14. As can be seen in FIGS. 2a-d, the first part of the gasket-type seal is provided by means of a projection 40 which extends out of the centre of the inner surface 42 of the first end 38 of the cap 6. Accordingly, when the cap 6 is placed over the barrel 4, the projection 40 extends into and blocks the distal end of channel 18 which connects the chamber 14 to the tip 20. As such, medicament cannot exit channel 18 while the cap 6 is secured on to the barrel 4. The inventors have found that a longer projection 40 is beneficial as it allows easier engagement with the channel 14 during application of the cap 6 and a larger surface area of engagement. Accordingly, in a preferred embodiment, the projection 40 has a length of about 3.43 mm.

Figure 1B:
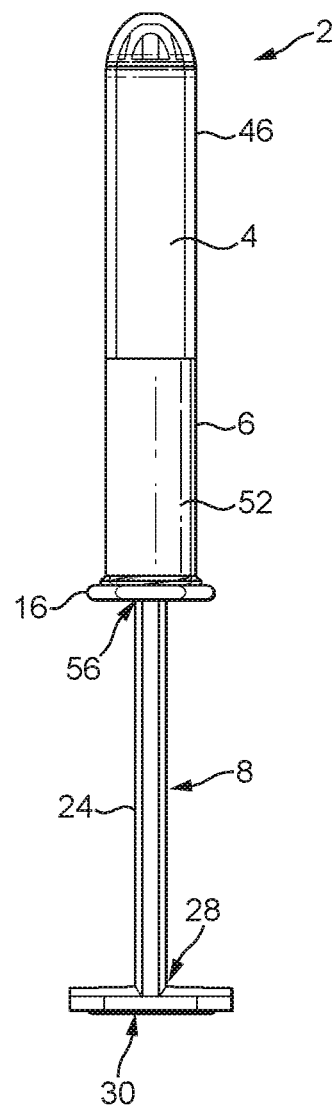
Figure 1C:
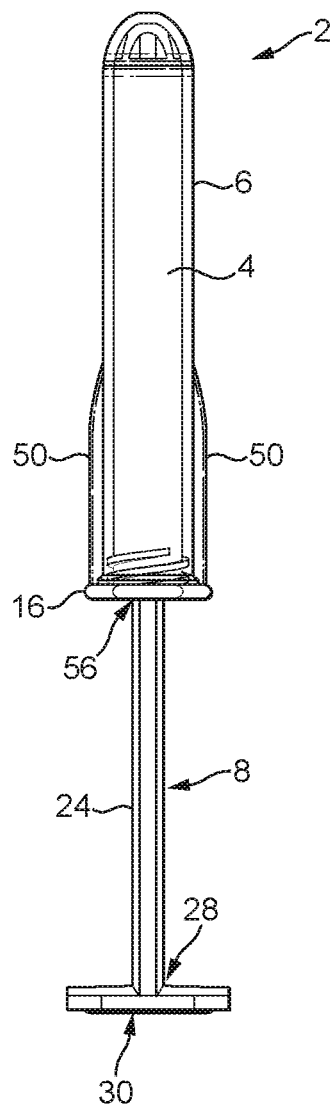
Figure 1D:
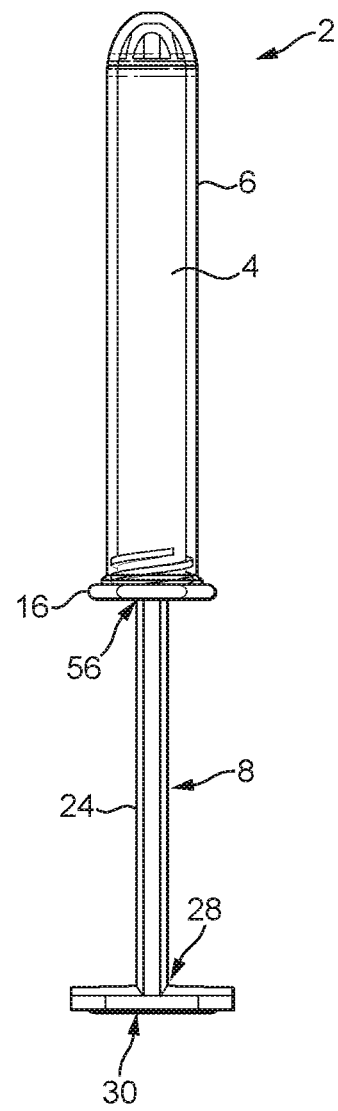

As can be seen in FIGS. 1a, 1c and 5, the second part of the gasket-type seal is provided by means of corresponding engaging screw threads 44 which are disposed on the outer surface of the second end 12 of the barrel 4, and also on the inner surface 42 of the second end 38 of the cap 6. These screw threads 38 mutually engage thereby ensuring that the cap 6 stays in place on the barrel 4 and enhancing the seal made between the projection 40 and the opening of channel 18, which further prevents leaking or unintentional discharge of medicament stored within the chamber 14 of the syringe 2. Additionally, as the screw threads 44 are spaced apart from the first end 10 of the barrel 4, they cannot come into contact with the mucous membrane in the mouth of a patient during drug administration, and so will not cause damage thereto during use.

The inventors have designed four different embodiments of outer cap 6. Firstly, in the embodiment of the syringe 2 shown in FIGS. 1d and 2d, the external surface 46 of the cap 6 is completely smooth. In the embodiment of the syringe 2 illustrated in FIGS. 1a and 2a, the external surface 46 of the second end 38 of the cap 6 is provided with a plurality of spaced apart elongated ridges 48, which extend along the longitudinal axis of the cap 6. These ridges allow a user to better grip the cap 6 at its second end 38 and thereby enable the user to quickly twist and unscrew the cap 6 and remove it from the barrel 4.

Figure 2A:
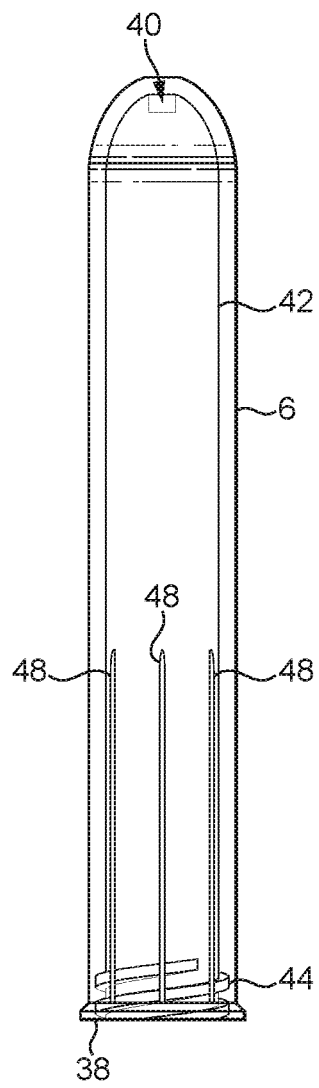
Figure 2B:
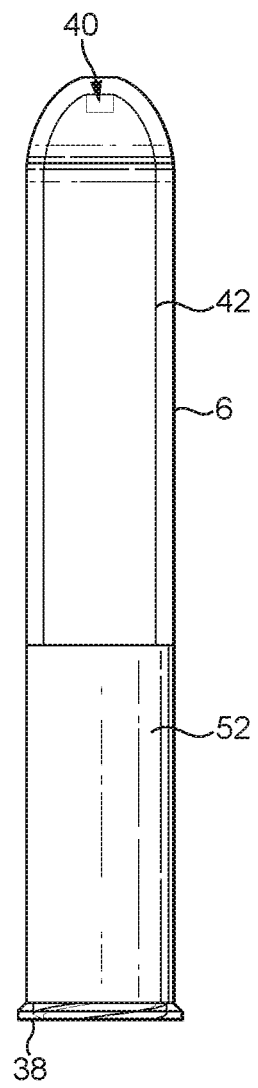
Figure 2C:
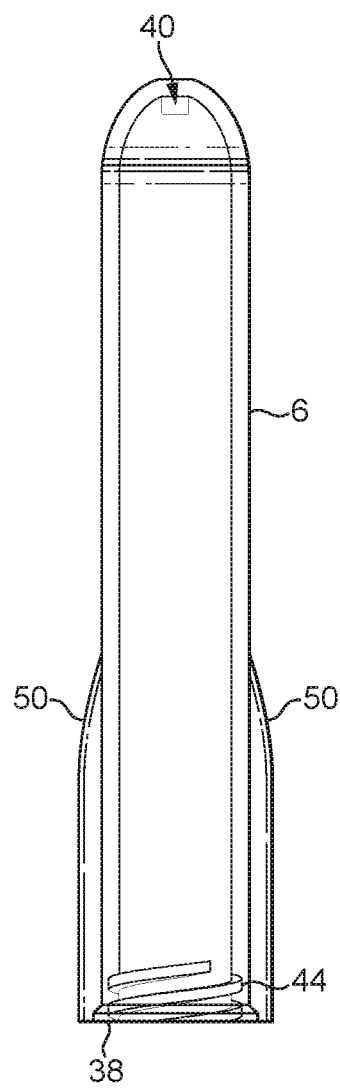
Figure 2D:
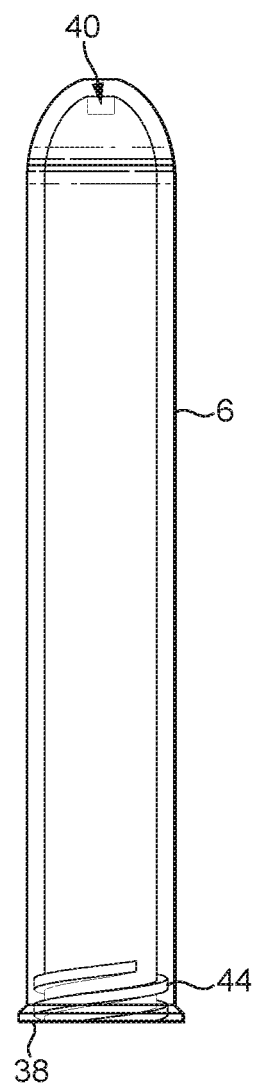
Figure 6A:
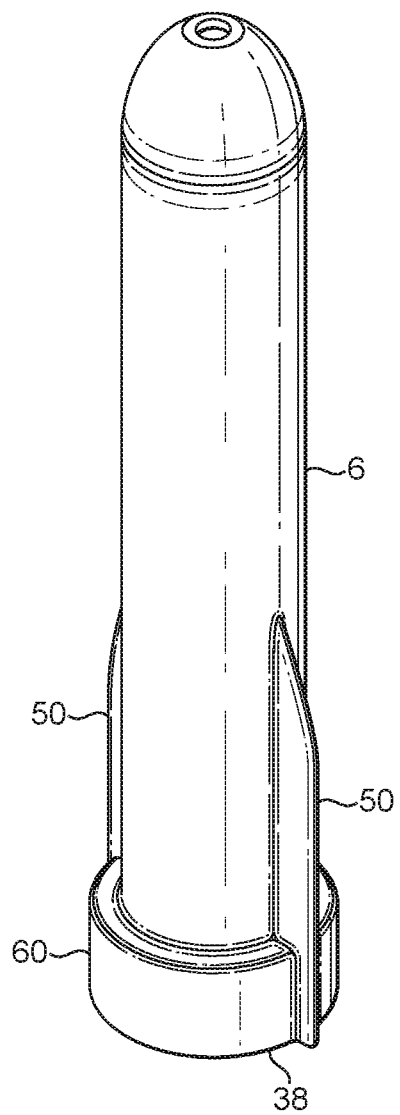
FIG. 6a is a perspective view of a further embodiment of an over sheath cap.
Figure 6B:
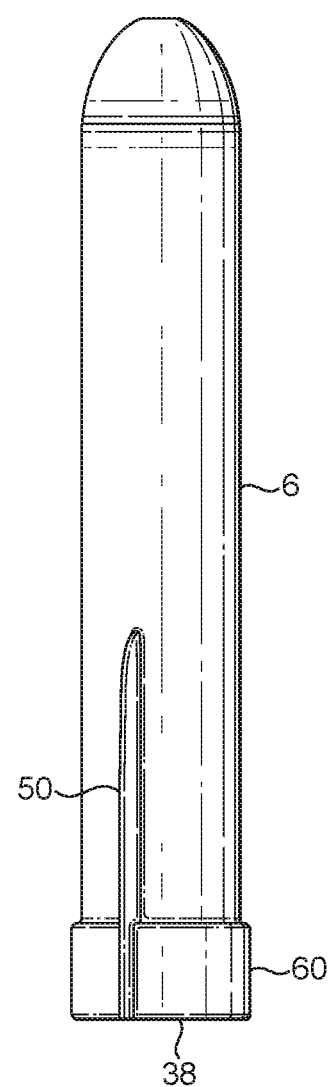
FIG. 6b is a side view of the further embodiment of the over sheath cap.

In the embodiment of the syringe 2 shown in FIGS. 1c and 2c, the second end 38 of the cap 6 has two transversely extending, external wings 50. The wings 50 are disposed on either side of the cap 6, and allow a user to better grip and unscrew the cap 6 from the barrel 4. Similarly, in the embodiment of the cap 6 shown in FIGS. 6a and 6b the cap also has two wings 50. In the embodiment illustrated, at its widest point the cap 6 has a width of 20.00 mm due to the wings. By way of comparison, the external diameter of the cap 6 over the majority of its height is 12.81 mm. Accordingly, each wing 50 extends a maximum of 8.10 mm from the side of the cap 6. The inventors have found that the larger wings 50 allow the cap 6 to be applied to the barrel 4 more easily using an automated process, and allow a user to grip the cap 6 more easily when they wish to remove it from the barrel 4. Additionally, the cap 6 also comprises a circumferential band 60 adjacent to the second end 38. The band 60 increases the diameter of the cap 6 adjacent to the second end 38, and in the preferred embodiment illustrated in FIGS. 6a and 6b the band 60 has a diameter of 17.50 mm. Accordingly, the band 60 increases the diameter of the cap 6 by 36.6% adjacent to the second end 38. The inventors have found that the presence of the circumferential band 60 and/or larger wings 50 allows the cap 6 to be released from a tool used to manufacture the pails. Accordingly, the band 60 and larger wings 50 promote longevity of the tool used to manufacture the parts.

As mentioned above, the finger tabs 16 have a maximum width of 25.40 mm. Accordingly, this is 98% greater than the diameter of the cap 6 and 75% greater than the band 60. Accordingly, when the cap 6 is in place over the barrel 4 the finger tabs 16 will extend beyond the edge of the cap 6 enabling easier removal of the cap 6 from the barrel 4.

In yet another embodiment, as shown in FIGS. 1b and 2b, the external surface 46 of the second end 38 of the cap 6 comprises a softened material 52, such as rubber. The softened material 52 allows a user to better grip the cap 6 and thereby unscrew it from the barrel 4.

Advantageously, the syringe 2 allows a medicament for buccal administration to be stored safely therein, without the risk of the medicament leaking or the solvent (e.g. ethanol) evaporating. Additionally, the medicament can be administered quickly to the patient without the user needing to pause to measure a dose. Additionally, the syringe 2 does not allow a user to attach the syringe 2 to a needle or drip and so removes any risk of a medicament intended for buccal administration being administered intravenously or intramuscularly, which could be dangerous.

The invention claimed is:

1. A syringe assembly comprising:
    a syringe barrel comprising an inner chamber filled or adapted to be filled with a medicament, and a channel in fluid communication with the chamber and through which the medicament is dispensed from a distal end of the barrel; and
    an outer sheath or cap, wherein the sheath or cap is a single contiguous structure configured to be removably attached to the syringe barrel, and comprising a projection disposed at a distal end of the sheath or cap, wherein the projection is received by the channel when the outer sheath or cap is attached to the barrel, thereby creating a first seal, which prevents medicament from flowing therethrough,
    wherein the syringe barrel comprises a single engagement means disposed on an external surface thereof and located at a proximal end of the barrel, which is opposite the distal end of the barrel, and wherein the outer sheath or cap comprises a single engagement means disposed on an internal surface thereof and located at a proximal end of the sheath or cap, which is opposite the distal end of the sheath or cap, whereby the syringe barrel single engagement means and the outer sheath or cap single engagement means are configured to mutually engage with each other in order to create a second seal, which prevents leakage or discharge of the medicament from the chamber when the outer sheath or cap is attached to the barrel, and wherein the distal end of the syringe barrel does not comprise attachment means for connection to a medicament transfer means.

2. A syringe assembly according to claim 1, wherein the attachment means is a projection and/or screw thread disposed at the distal end of the syringe barrel.

3. A syringe assembly according to claim 1, wherein the engagement means comprise screw threads.

4. A syringe assembly according to claim 1, wherein the syringe assembly is for administering medicament orally, buccally, sublingually, rectally, vaginally, topically or transdermally.

5. A syringe assembly according to claim 1, wherein the syringe assembly is a buccal syringe assembly, which is used for administering the medicament to a patient's buccal cavity.

6. A syringe assembly according to claim 1, wherein the syringe barrel is incompatible with a Luer lock or Luer slip.

7. A syringe assembly according to claim 1, wherein the syringe barrel does not comprise an external screw thread at the distal end.

8. A syringe assembly according to claim 1, wherein the distal end of the barrel comprises a plurality of spaced apart flanges, which extend from a side wall of the barrel and converge at the dispensing tip of the barrel to define an aperture which leads to the channel through which the medicament is dispensed, preferably wherein adjacent flanges are the same length so as to produce a substantially smooth profile.

9. A syringe assembly according to claim 1, wherein the barrel comprises a transparent or translucent material.

10. A syringe assembly according to claim 1, wherein the outer sheath or cap is configured to be removably attached to the syringe barrel to thereby encase at least a portion of the chamber, and preferably all of the chamber.

11. A syringe assembly according to claim 1, wherein the outer sheath comprises an opaque material and/or an amber coloured material.

12. A syringe assembly according to claim 1, wherein an external surface of the outer sheath is substantially smooth.

13. A syringe assembly according to claim 1, wherein an external surface of the outer sheath or cap comprises one or more projections which extends transversely therefrom, and which is configured to facilitate removal of the outer sheath from the barrel, preferably wherein an external surface of the outer sheath comprises a plurality of spaced apart elongate ridges or protrusions, which extend along the longitudinal axis of the outer sheath or cap.

14. A syringe assembly according to claim 1, wherein at least a portion of the external surface of the outer sheath or cap comprises a softened material, such as rubber or a suitable thermoplastic elastomer.

15. A syringe assembly according to claim 1, wherein the syringe assembly is a single unit dose syringe assembly pre-filled with the medicament.

16. A syringe assembly according to claim 1, wherein the medicament is selected from a group of medicaments consisting of: analgesics, anti-convulsants, antidepressants, vasodilators, steroids, opiate antagonists, anaesthetics, antiadrenergic compounds, antiallergic drugs, anti-anginals, antiasthmatics, antibacterials, anti-coagulants, anti-cholinergics, antiemetics, antiepileptics, antihistaminics, antiinfectives, antiinflammatories, antimigraine drugs, bronchodilators, cardiac depressants, thrombolitics, beta blockers, opioids, sedatives, benzodiazepines and stimulants.

17. A syringe assembly according to claim 1, wherein the medicament is selected from a group consisting of: midazolam, lorazepam, diazepam, paraldehyde, pentobarbital, morphine, carbamazepine, ethosuximide, clorazepate, clonazepam, felbamate, forphenytoin, gabapentin, lacosamide, lamotrigine, levetiracetam, oxacarbacepine, phenobarbital, phenytoin, pregabalin, primidone, tiagabine, topiramate, zonisamide, clobazam, vigabatrin, fentanyl, oxycodone, diamorphine, alprazolam, clonazepam, vasopressin, levetiracetam, and NSAIDs, or a salt thereof.

18. A syringe assembly according to claim 1, wherein the syringe assembly is a unit dose syringe assembly pre-filled with midazolam or a salt thereof, such as midazolam maleate.

19. A syringe assembly according to claim 1, wherein the syringe assembly comprises a plunger configured to slide in the chamber, preferably wherein the plunger comprises a rod having first and second ends, wherein the first end is inserted into the chamber, and the second end comprises a thumb tab, and the barrel comprises a finger tab, which is configured to be engaged with the finger of one hand while also engaging the thumb tab with the thumb of the same hand, more preferably wherein the syringe assembly comprises a transversely extending projection disposed on the side of the plunger rod, and an indentation disposed along the inside of the chamber, or vice versa, wherein alignment of the projection and indentation correlates with a defined volume of medicament and thereby a dosage.

20. A syringe assembly according to claim 1, wherein the chamber is adapted to hold about 0.1-25 ml, or about 0.1-10 ml, or about 0.1-5 ml, or about 0.1-2 ml, or about 0.1-1 ml of the medicament.

* * * * *